United States Patent [19]

Gunther

[11] 4,066,399
[45] Jan. 3, 1978

[54] METHOD FOR HUMIDIFYING A GAS STERILIZER

[75] Inventor: Donald A. Gunther, Erie, Pa.

[73] Assignee: American Sterilizer Company, Erie, Pa.

[21] Appl. No.: 617,244

[22] Filed: Sept. 26, 1975

Related U.S. Application Data

[62] Division of Ser. No. 262,313, June 13, 1972, Pat. No. 3,936,270.

[51] Int. Cl.² .......................... A61L 1/00; A61L 3/00; A61L 13/00; A23L 3/34
[52] U.S. Cl. ............................................ 21/58; 21/57; 21/DIG. 4; 21/91; 261/78 A; 426/320; 426/335
[58] Field of Search ................. 21/56, 57, 58, DIG. 4, 21/91; 261/78 A; 426/320, 335

[56] References Cited

U.S. PATENT DOCUMENTS

| 903,853 | 11/1908 | Gartner | 21/57 |
|---|---|---|---|
| 1,754,251 | 4/1930 | Yates | 21/57 |
| 1,791,429 | 2/1931 | Roark et al. | 21/57 X |
| 2,297,230 | 9/1942 | Langen | 21/57 X |
| 2,921,832 | 1/1960 | Holther | 21/53 |
| 3,068,064 | 12/1962 | McDonald | 21/58 |
| 3,257,161 | 6/1966 | Kaye | 21/58 |
| 3,481,689 | 12/1969 | Rosdahl et al. | 21/58 |
| 3,489,505 | 1/1970 | Schumann et al. | 21/91 |
| 3,490,863 | 1/1970 | Schumann et al. | 21/58 |
| 3,503,703 | 3/1970 | McDonald et al. | 21/91 |
| 3,598,516 | 8/1971 | Shull et al. | 21/58 X |

FOREIGN PATENT DOCUMENTS

| 488,638 | 7/1938 | United Kingdom | 426/320 |
|---|---|---|---|

OTHER PUBLICATIONS

Kaye, Am. J. Hyg., 1949, vol. 50, pp. 296-306.
Schley, Applied Microbiology, vol. 8, No. 1, Jan. 1960, pp. 1-4, 15-19.
Phillips, Am. J. Hyg., 1949, vol. 50, pp. 270-279.
Rauscher, Food Manufacture, Apr. 1957, pp. 169-172.

*Primary Examiner*—Stephen J. Emery
*Attorney, Agent, or Firm*—Shanley, O'Neil and Baker

[57] ABSTRACT

Humidifying composition is introduced into a portable gas sterilizer in droplet form. The composition is packaged in an aerosol can and comprises water, preferably water and organic solvent. Automatic controls effect a predetermined relative humidity in the sterilizer before initiating sterilizing gas introduction.

4 Claims, 2 Drawing Figures

METHOD FOR HUMIDIFYING A GAS STERILIZER

This is a division, of application Ser. No. 262,313, filed June 13, 1972 now U.S. Pat. No. 3,936,270, issued Feb. 3, 1976.

BACKGROUND OF THE INVENTION

This invention relates to gas sterilization and in particular to such sterilization in a portable sterilizer.

Gas sterilizers are typically utilized for example in hospitals for treating articles, for example of plastic, paper, rubber or the like which cannot withstand heat sterilization. Sterilization is effected when gaseous sterilizing agent reacts with contaminating microorganisms to kill or inactivate them. The most popular sterilizing agent presently employed is ethylene oxide in admixture with an inert diluent such as dichlorodifluoromethane.

The aforementioned reaction is carried out most effectively with the aid of a reaction solvent, typically water. It is theorized that the reaction solvent forms a coating on a microorganism, and the reaction occurs in this coating at the microorganism surface. The introduction of the reaction solvent into the sterilizer is referred to in the art as humidification.

In larger permanently emplaced sterilizers, humidification is expediently accomplished by introduction of low-pressure steam. However, in small (for example, ½ to 3 cubic feet), portable sterilizers, it is not feasible to connect a steam line for humidification purposes. For portable sterilizers the most common method of humidification comprises pouring a measured amount of water on the sterilizer floor after loading and just prior to closing the sterilizer door and initiating ethylene oxide introduction; this method is referred to as "puddling".

The puddling method has disadvantages. Firstly, it is slow. The water must vaporize from the puddle in order to be distributed through the load and penetrate to the microorganisms. This takes time. Secondly, this method relies on the operator to remember to add the water.

A main object of this invention is the provision of a system and method whereby humidification is carried out so that a significant savings in time is achieved. Another object is to provide a system which minimizes reliance on an operator for humidification and produces a precise predictable humidity level from run to run. Still another object of one very preferred embodiment of the invention is the provision of a more effective humidification composition.

These objects and others will be evident from the following detailed description.

BRIEF DESCRIPTION OF THE DRAWINGS

In describing preferred embodiments of the invention, reference is made hereinafter to the accompanying drawings in which.

DESCRIPTION OF PREFERRED EMBODIMENT

Figure 1:
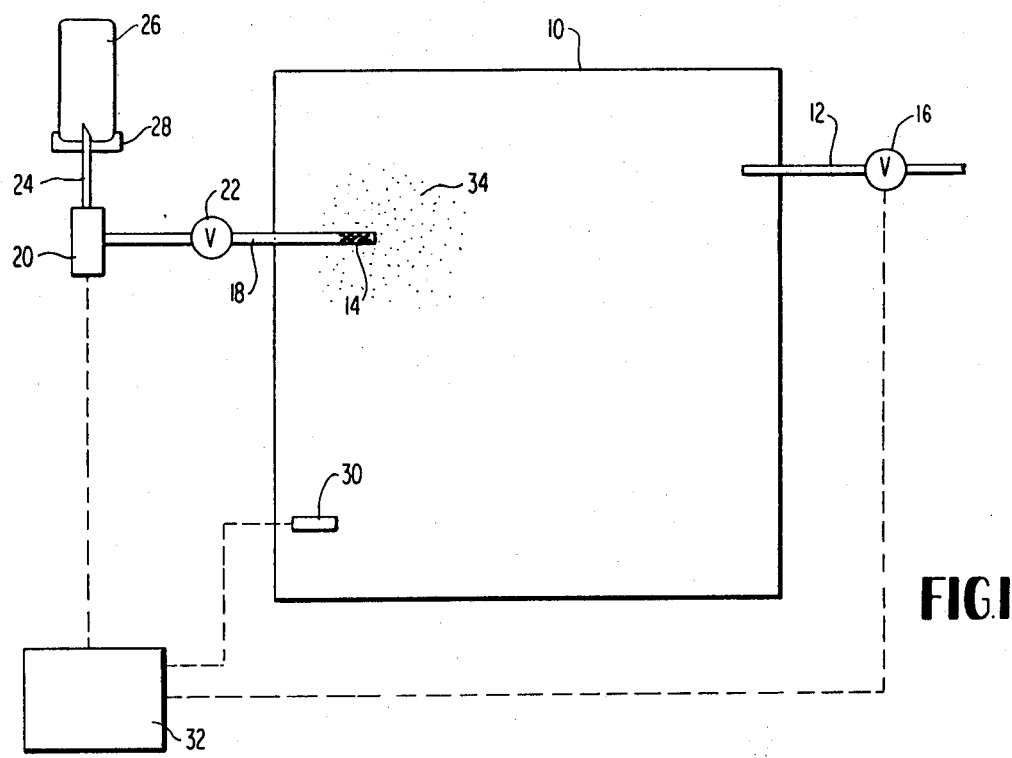
FIG. 1 is a schematic diagram of the system of a preferred embodiment of the invention.

Referring to FIG. 1, a preferred embodiment of a sterilizing system within the scope of the present invention includes a sterilizing chamber 10 having an ethylene oxide introduction conduit 12 and humidification atomizing nozzle 14 in the form of a pipe with holes drilled in it communicating therewith. Conduit 12 contains a solenoid-operated valve 16. A conduit 18 communicates with nozzle 14. It communicates at its upstream end with a solenoid-operated valve 20 and contains a metering valve 22. Communicating with conduit 18 through valve 20 is a conduit 24. This conduit has a longitudinal axis which is vertically oriented and has its upstream end beveled to provide puncturing means and has its outer surface at its upstream end threaded to threadably receive an aerosol container to be punctured. Such an aerosol container is shown in place denoted by reference numeral 26. Conduit 24 carries a can support 28 which is adapted to receive and provide a seat for can 26. A pressure sensing means in the form of a diaphragm 30 is positioned inside chamber 10. A controller 32 including a pressure sensitive switch operates in response to diaphragm 30 to generate signals for the operation of solenoid-operated valves 16 and 20.

The aerosol container 26 is pressurized to a relatively low pressure, e.g. 15 p.s.i.g. It contains humidifying composition and a propellant. The humidifying composition is discussed in detail below. Suitable propellants are well known in the aerosol art. Preferably, the propellant is dichlorodifluoromethane inasmuch as this component is conventionally introduced into the system. A container 26 holds sufficient humidifying composition and propellant for a number of sterilizing cycles, e.g. 30 cycles. It is connected into the system by engaging a threaded portion on conduit 24 and screwing down so that the container is punctured and is supported on structure 28. When used up, container 26 is disconnected from the system by unscrewing and a fresh container is connected. When the sterilizer is not being operated, flow into chamber 10 is prevented by valve 20 which is normally in closed position.

In practice, chamber 10 is loaded with articles to be sterilized and the door to it (not depicted) is closed. Then controller 32 is activated. Such activation can be automatic responsive to the closing of the door of chamber 10 or can be manual utilizing a switch in the system energizing controller 32. Controller 32 then signals valve 20 to open and the pressure head in container 26 forces the humidifying composition therein through conduits 24 and 18 and such fluid emits from atomizing nozzle 14 in droplet form, for example as a mist or fine spray, denoted by reference numeral 34. The sprayed particles rapidly evaporate and the vapor penetrates to the microorganisms in the load being sterilized. Metering valve 22 is provided to slow the entry of humidifying composition into chamber 10 so as to permit humidification over a time period such that maximum penetration to the microorganisms in the load is achieved. Valve 22 is an optional component in the system but is quite desirable as it permits precise control over the humidification process. While the optimum time period for introduction of the humidifying composition into chamber 10 will depend upon the loading density in the chamber and the type of articles loaded (whether they are easy or hard to penetrate), a typical time would be 15 minutes and the metering valve 22 can be set to provide a time on this order.

When the predetermined degree of humidifying has been achieved in chamber 10, this is sensed by element 30 as the relative humidity in the chamber is directly proportional to the pressure in the chamber. Controller 32 thereupon signals valve 20 to close and at the same time signals valve 16 to open. Upon opening of valve 16, ethylene oxide is introduced into chamber 10 and the sterilization cycle is begun.

The above system and method has the advantage of providing the humidification composition into the chamber in droplet form so that it can rapidly evaporate and have a chance to penetrate to the microorganisms in time for the sterilization cycle. It delivers a precise predetermined quantity of the contents at the optimum time in the sterilization cycle, that is at the beginning of the cycle. It assures that the proper humidity level is achieved without relying upon the memory of the operator or the operator's skill in measuring or estimating the amount of water to be added. Moreover, it assures that the sterilization cycle will not be started unless a proper humidification level is present thereby assuring that sterilization will not fail because of improper humidification.

While the above system and method provides significant advantage over the puddling method when the humidifying composition is water alone, it has been discovered that a further significant improvement is achieved when the humidifying composition comprises water and organic solvent. The organic solvent which has been found useful for this very preferred embodiment is one that is water soluble and whose presence increases the vapor pressure, decreases the surface tension and lowers the polarity of the humidifying composition. It has been surprisingly discovered that the inclusion of such an organic solvent improves the permeability of the humidifying composition through the pores of the articles being sterilized thereby increasing the probability of the water reaching the microorganisms and thereby increasing sterilization efficiency. The inclusion of such solvent also increases the wetting ability of the humidifying composition thereby increasing sterilization efficiency.

With respect to the percentage of such solvent in the humidifying composition, the upper limit is that amount which is soluble in water. It is to be recognized that very low percentages of solvent will have only slight effect, and that very high percentages may require large amounts of humidifying composition to achieve a particular relative humidity.

Suitable organic solvents are selected, for example, from the group of lower ($C_1 - C_4$) alcohols, ketones and ethers. For example, lower alcohols such as methanol, ethanol, isopropanol and n-butanol are quite suitable for use herein. A suitable ketone is acetone and a suitable ether is diethyl ether. Isopropanol and n-butanol are the most preferred organic solvents.

The advantage over the puddling method of humidifying a portable gas sterilizer by introducing water in droplet form and the further advantage of utilizing a humidifying composition consisting not only of water but also of particular organic solvents is shown in the following example.

EXAMPLE

The sterilizer utilized is a portable gas sterilizer having a volume of approximately one cubic foot. An electronic humidity sensor is loosely wrapped with polyethylene film of two mils thickness. The sensing element is approximately one inch in diameter and three to four inches long. It is positioned on a rack at the geometric center of the sterilizer.

Four runs are carried out. In Run A humidifying is carried out by the puddling method, and the humidifying composition consists of water. In Runs B, C and D humidifying is carried out by atomizing, that is aerosoling, humidifying composition into the sterilizer in droplet form. In Run B the humidifying composition consists of water. In Run C the humidifying composition consists by volume of 50% isopropanol and 50% water. In Run D the humidifying composition consists by volume of 5% n-butanol and 95% water. In each run an amount of humidifying composition is introduced to provide a relative humidity of 100% in the sterilizer. In each run the sterilizer is maintained at 130° F. which is a typical gas sterilizing temperature.

Puddling is carried out by filling a measured amount of water into a graduated cylinder and dumping on the sterilizer floor. For atomizing, a hypodermic syringe is utilized with a needle bent so as to supply droplets; the needle is pierced through a septum in the sterilizer wall and the proper amount of humidifying composition injected.

Figure 2:
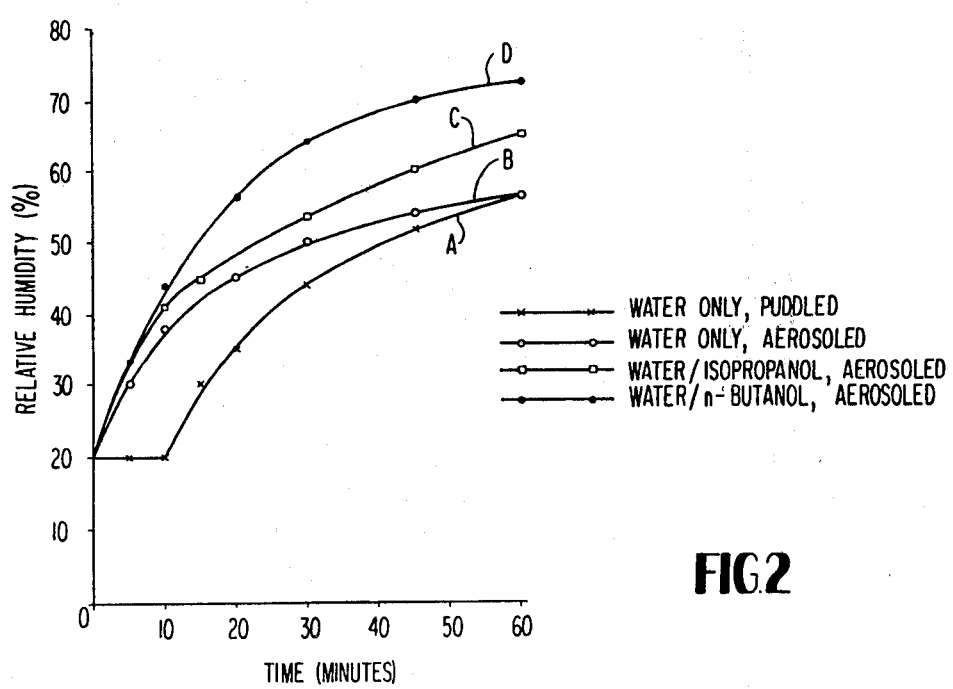
FIG. 2 is a graph as more fully described in an example hereinafter and depicts the advantage of various embodiments of the invention over the commonly used puddling method.

Humidity readings are taken at various time intervals, and the relative humidity at the various times is plotted for each run with results as depicted in FIG. 2. Referring to the graph of FIG. 2, Curve A depicts the results of Run A, Curve B corresponds to Run B, Curve C to Run C and Curve D to Run D.

The graph shows that with water only, 50% relative humidity is achieved with aerosoling in approximately 30 minutes (Curve B) as compared to over 40 minutes where water only is puddled (Curve A) indicating a time advantage of over 25% for the run within the scope of the invention over the run carried out conventionally. In Run C, a 50% relative humidity is achieved in about 24 minutes and in Run D in about 15 minutes thereby demonstrating a further significant advantage where the humidifying compositions including organic solvent are utilized. The 50% relative humidity level used for comparison purposes, is a very typical humidity level used in gas sterilizing.

In view of the variations that are readily understood to come within the limits of the invention, such limits are defined by the scope of the appended claims.

I claim:

1. In a gas sterilization process carried out in a sterilizing chamber and involving humidification of materials within the chamber and subsequently involving introduction of sterilizing gas, the steps comprising
    a. providing improved humidification by
        i. providing a combination of water and water soluble organic solvent whose presence increases vapor pressure, decreases surface tension and lowers polarity, said solvent being selected from the group consisting of lower alcohols, ketones and ethers; and
        ii. introducing such combination of water and organic solvent into the sterilizing chamber, the presence of the organic solvent improving the permeability of such combination through the pores of materials within such chamber; and
    b. subsequent to step (a), introducing into the sterilization chamber sterilizing gas comprising ethylene oxide.

2. Method as recited in claim 1 in which the combination is introduced into the sterilizing chamber in droplet form.

3. Method as recited in claim 1 in which the organic solvent is isopropanol.

4. Method as recited in claim 1 in which the organic solvent is n-butanol.

* * * * *